US00PP23175P2

(12) United States Plant Patent
Gray et al.

(10) Patent No.: US PP23,175 P2
(45) Date of Patent: Nov. 13, 2012

(54) ROSE PLANT NAMED 'GRASUPER'

(50) Latin Name: ***Rosa* hybrid**
Varietal Denomination: GRAsuper

(76) Inventors: John Gray, Highfields (AU); Sylvia E. Gray, Highfields (AU)

( * ) Notice: Subject to any disclaimer, the term of this patent is extended or adjusted under 35 U.S.C. 154(b) by 0 days.

(21) Appl. No.: 13/134,083

(22) Filed: May 27, 2011

(51) Int. Cl.
*A01H 5/00* (2006.01)

(52) U.S. Cl. ..... Plt./141; Plt./148

(58) Field of Classification Search ..... Plt./137, Plt./148, 141
See application file for complete search history.

*Primary Examiner* — Kent L Bell
(74) *Attorney, Agent, or Firm* — Cassandra Bright

(57) ABSTRACT

A new and distinct floribunda type *Rosa* hybrid named 'GRAsuper' is disclosed, characterized by complete resistance to *Diplocarpon rosae* and continuous flowering. Plants produce pink flowers with a strong fragrance and typically reach a height of between 1 to 1.2 meters. The new cultivar is a *Rosa* typically suited for ornamental container and landscape use.

2 Drawing Sheets

Latin name of the genus and species: *Rosa* hybrid.
Variety denomination: 'GRAsuper'.

BACKGROUND OF THE INVENTION

The new cultivar is the result of a chance discovery in a commercial nursery in Highfields, Queensland, Australia. The inventors, John Gray and Sylvia Gray, citizens of Australia, discovered the new variety as a single whole plant mutation of the parent variety, a floribunda type *Rosa* hybrid, 'CHEWfragbabe', unpatented in the United States. The discovery was made October , 2009.

After selecting the new cultivar, asexual reproduction of 'GRAsuper' was first performed in the same commercial nursery by vegetative cuttings March 2010. 'GRAsuper' has since produced two generations and has shown that the unique features of this cultivar are stable and reproduced true to type.

SUMMARY OF THE INVENTION

The cultivar 'GRAsuper' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GRAsuper'. These characteristics in combination distinguish 'GRAsuper' as a new and distinct *Rosa* hybrid cultivar:

1. Complete resistance to the fungus *Diplocarpon rosae.*
2. Repeat flowering.
3. Plant height between 1 to 1.2 meters.
4. Strong fragrance.
5. Pink flower color.

PARENTAL COMPARISON

Plants of the new cultivar 'GRAsuper' are similar to the parent, *Rosa* hybrid 'CHEWfragbabe' in most horticultural characteristics. However, 'GRAsuper' differs in flower color.

Flowers of the parent variety are white with champagne colored centers, whereas plants of the new variety produce pink flowers.

COMMERCIAL COMPARISON

Plants of the new cultivar 'GRAsuper' can be compared to the unpatented commercial variety *Rosa* hybrid 'Iceberg'. 'GRAsuper' differs from 'Iceberg' in its complete resistance to *Diplocarpon rosae*. Additionally, 'GRAsuper' has more petals per flower, and new foliage with a blue-purple blush not found on 'Iceberg'. The two varieties also differ in flower color, and 'GRAsuper' has a stronger scent than 'Iceberg'.

Plants of the new cultivar 'GRAsuper' can be compared to the commercial variety *Rosa* hybrid 'MEIbeausai', U.S. Plant Pat. No. 7,667. 'GRAsuper' differs from 'MEIbeausai' in its complete resistance to *Diplocarpon rosae*. Additionally, 'GRAsuper' has smaller new foliage, with serrate margins and a distinctive blue-purple blush on the new foliage not found on 'MEIbeausai'. 'GRAsuper' also has a stronger scent than 'MEIbeausai'.

BRIEF DESCRIPTION OF THE PHOTOGRAPHS

Figure 1:
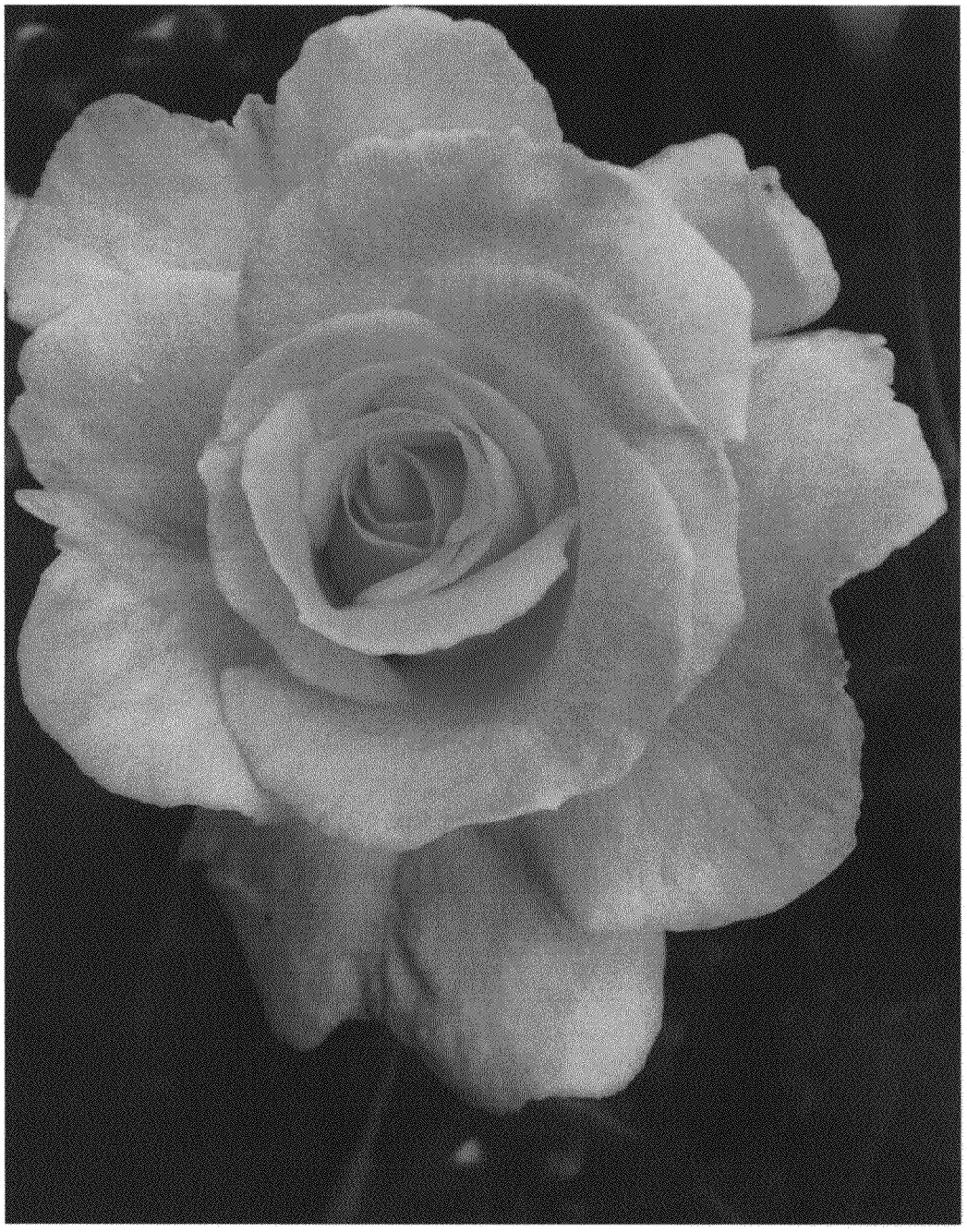

The accompanying photograph in FIG. 1 illustrates in full color a typical flower of 'GRAsuper' grown outdoors in Highfields Australia.

Figure 2:
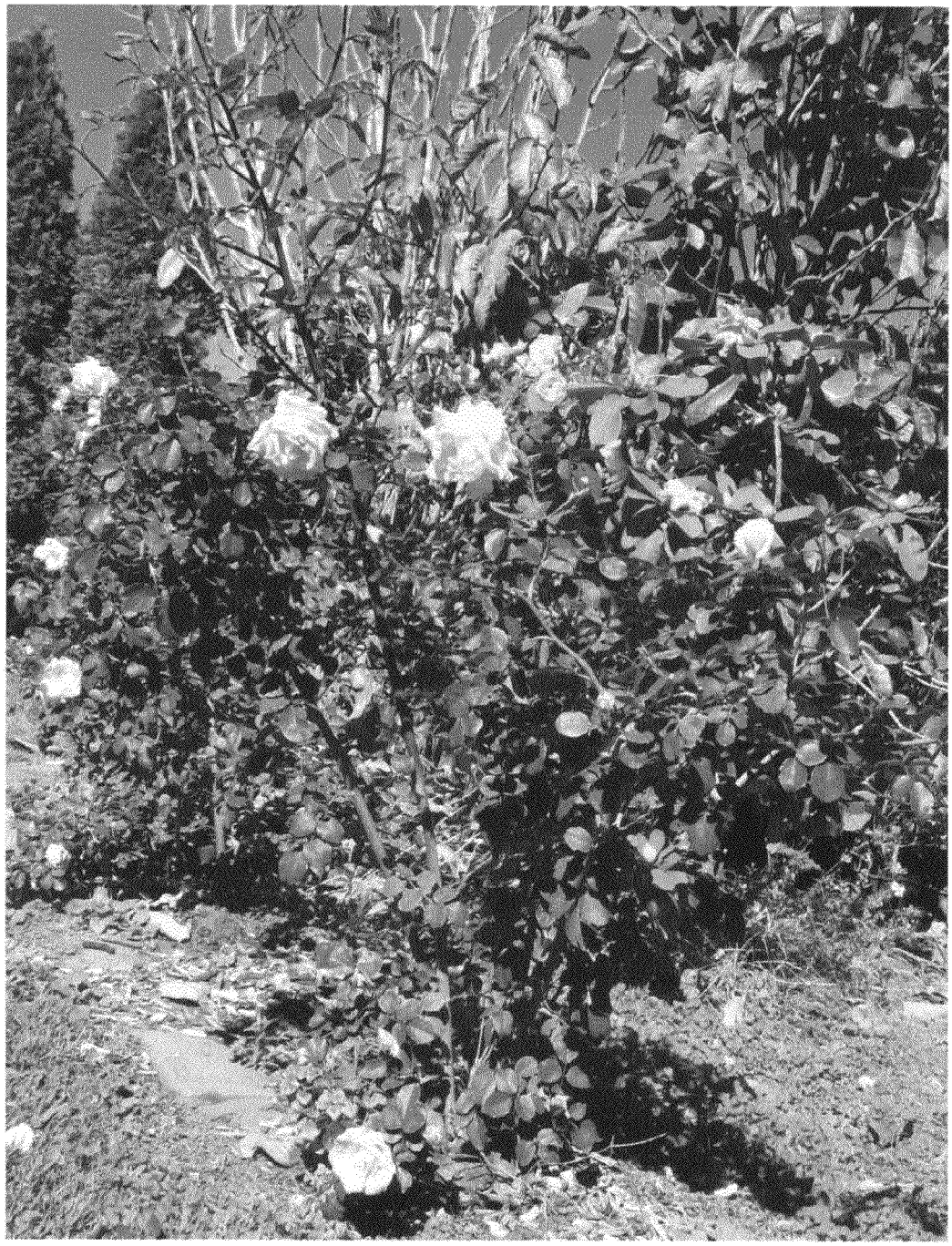

FIG. 2 illustrates in full color a typical plant of 'GRAsuper' grown outdoors in Highfields Australia. The plant is approximately 12 months old. The photograph was taken using conventional techniques and although colors may appear different from actual colors due, to light reflectance it is as accurate as possible by conventional photographic techniques.

DETAILED BOTANICAL DESCRIPTION

In the following description, color references are made to The Royal Horticultural Society Colour Chart 1995, except where general terms of ordinary dictionary significance are used. The following observations and measurements describe 'GRAsuper' plants grown in Clyde, Victoria, Australia, described during the Fall. Plants were grown in 20 cm containers in a soilless pine bark media, inside an open polythene covered greenhouse, with 70% shade. Ventilation was very good, plant nutrition was by liquid feed from a hydroponic solution designed for roses as required, generally every 1-2 days. The growing temperature ranged from 8° C. to 14° C. at night to 18° C. to 23° C. during the day. From the initial eye, the first generation was cut 10-20 cm. The second generation was allowed to flower with the lateral shoots (third generation) being left to flower from which the observations were made. No artificial light, photoperiodic treatments or chemical treatments were given to the plants. Measurements and numerical values represent averages of typical flowering types.

Botanical classification: *Rosa* hybrid 'GRAsuper'.

Age of the plant described: Approximately 10 months.

Container size of the plant described: 20 cm commercial container.

PROPAGATION

Typical method: Vegetative cuttings.

Time to rooting: Approximately 9 days at 20° C.

Time to produce a rooted plantlet: Approximately 21 days at 20° C.

Root description: Well branched, fibrous with many root hairs extending from lesser roots in a feather like arrangement.

PLANT

Growth habit: Spreading with 4-5 breaks from the original bud.

Height: Approximately 45-55 cm.

Plant spread: Approximately 55-65 cm.

Rootstock: 'Natal Briar'.

Growth rate: Approximately 1 years to reach 0.5 meters.

Branching characteristics: Irregular branching from mature stems from bud eyes towards the apex of each shoot.

Length of primary lateral branches: Approximately 20 cm.

Diameter of lateral branches: Approximately 0.5 cm.

Quantity of lateral branches: Numerous.

Branching arrangement: Random, breaking from upper most eyes first, with the first 4-5 buds producing lateral flowers. The subsequent 2-3 buds producing new lateral flowering stems.

Branches — young wood:

*Diameter*.—Approximately 0.3 cm.

*Texture*.—Smooth.

*Approximately density/quantity of thorns*.—Approximately 3 to 5 thorns per 10 linear cm of stem, on the lower half of stem. Thorn density decreases towards the upper portion of stem, becoming highly infrequent, to no thorns present.

*Color*.—Near RHS Greyed-Purple 184A at top where anthocynanin coloration is present, Yellow-Green 145A at lower end. Anthocyonin colored near Greyed-Purple 184A.

Branches — old wood:

*Diameter*.—Approximately 1 cm, after 1 year.

*Texture*.—Smooth.

*Approximately density/quantity of thorns*.—Approximately 3 to 5 thorns per 10 linear cm of stem.

*Color*.—Near RHS Green143C.

Thorn description:

*Average height*.—6 mm.

*Average length*.—10 mm.

*Shape*.—Slight concave angling downward.

*Color*.—Immature: near RHS Greyed-Red 178A. Mature: near RHS Gren 143A, flushed Greyed-Red 178A.

FOLIAGE

Leaf:

*Arrangement*.—Alternate, compound.

*Quantity*.—Approximately 8 per main branch.

*Leaflets and rachis*.—3 leaflets per leaf for the upper most leaves, 5 & 7 leaflets in relatively even quantities for the rest, generally with more 7 leaflet leaves towards the base on stronger stems. Rachis length between the terminal and the secondary leaflet pairs are between 9 and 24 mm with an average of 17 mm which remains consistent between the secondary and tertiary leaflet pairs and again between the next set of leaflets when the leaf is a 7 leaflet leaf. The length of the Rachis to these leaflet pairs was 2 mm. Rachis colored near RHS Green 137D.

*Average length*.—Approximately 5 cm (terminal leaflet).

*Average width*.—Approximately 3.7 cm (terminal leaflet).

*Shape of blade*.—Broad ovate.

*Apex*.—Acute.

*Base*.—Rounded.

*Margin*.—Evenly serrate.

*Texture of top surface*.—Glabrous, ribbed along vein lines.

*Texture of bottom surface*.—Glabrous, ribbed along vein lines.

*Pubescence*.—Non-pubescent.

*Leaf internode length*.—Average 2.5 cm.

*Color*.—Young foliage upper side: Near RHS Green 137C, flushed with Greyed-Purple 187A. Young foliage under side: Near RHS Yellow-Green 146C flushed with Greyed-Purple 187A. Mature foliage upper side: Near RHS Green 139A. Mature foliage under side: Near RHS Yellow-Green 147B.

*Venation*.—Type: Pinnate. Venation color upper side: Near Green 139A. Venation color under side: Near Yellow-Green 147B.

*Petiole*.—Length: 2 cm. Width: 1.5 cm. Color: Near RHS Yellow-Green 147A. Texture: Tiny hairs to smooth.

*Stipule*.—Description: 1 to 2 per leaf, slightly concave. Length: 10 mm. Width: 2 mm. Color: Near RHS Yellow-Green 147B.

FLOWER

Natural flowering season: Continuous repeat flowering from October to June in the Southern Hemisphere.

Begins flowering after how many years/months: 6-8 weeks for the stem to grow and mature. Flowering occurs once stem matures. First flowers 6-8 weeks from cutting/budded eye to break.

Inflorescence type and habit: Double, irregularly rounded with loose petal whorl.

Rate of flower opening: Approximately 6 days from bud to fully opened flower.

Flower longevity on plant: 9 days, after fully opened.

Quantity of flowers: 4-7 per stem.

Inflorescence size:

*Diameter*.—Approximately 8.5 cm.

*Depth*.—Approximately 3.9 cm. (Flower height).

Peduncle:
*Length*.—Approximately 0.6 cm.
*Diameter*.—Approximately 0.3 cm.
*Color*.—Near RHS Green 137A.

Petals:
*Petal arrangement*.—Loose, irregular whorl.
*Size*.—Length: Approximately 3.8 cm. Width: Approximately 3.5 cm.
*Shape*.—Obovate.
*Margin*.—Slight undulation, slight reflexing at apex.
*Apex*.—Rounded to cordate.
*Base*.—Flattened then obtuse.
*Petal quantity*.—Average 46.
*Texture*.—Fine.
*Aspect*.—Slightly ruffled.

Color: Petals: When opening: Upper surface: Near RHS Red-Purple 62C. Lower surface: Near RHS White 155A. Fully opened: Upper surface: Near RHS Red-Purple 69D. Lower surface: Near RHS White 155A. Color Changes when aging: Fades to near RHS White 155C as open flower matures.

Bud:
*Shape*.—Ovate.
*Length*.—Approximately 2.5 cm.
*Diameter*.—Approximately 1.4 cm.
*Color*.—Near RHS Green 143C.
*Sepals*.—Length: Approximately 3 cm. Width: Approximately 0.8 cm. Shape: Lanceolate. Apex: Moderately apiculate, with the apex extensions occurring mostly singular, occasionally double, without feathering appearance. Margin: Mostly entire, with occasional weak dentation. Color. Interior Surface: RHS Yellow-Green 147C. Exterior Surface: RHS Green 143B.
*Texture*.—Densely puberulent.

Receptacle:
*Length*.—0.7 cm.
*Width*.—0.7 cm.
*Shape*.—Pitcher shaped.
*Color*.—Green, actual RHS color indeterminable.

Fragrance: Strong, citrus-like scent.

REPRODUCTIVE ORGANS

Stamens:
*Number*.—Approximately 50.
*Filament length*.—Approximately 0.7 cm.
*Filament color*.—Yellow, RHS color indeterminable.

Anthers:
*Length*.—0.2 cm.
*Shape*.—Narrow ovate.
*Color*.—Near RHS Yellow-Orange 21B.
*Pollen*.—Color: Yellow, RHS color indeterminable. Quantity: Abundant.

Pistil:
*Number*.—Approximately 50.
*Length*.—Approximately 2 cm.
*Style*.—Length: Approximately 0.8 cm. Color: Near RHS Yellow-White 158C.
*Stigma*.—Shape: Ovate. Color: Near RHS Yellow 11B.

OTHER CHARACTERISTICS

Seeds and fruits: Not observed at the time of description.

Disease/pest resistance: Excellent tolerance to fungal diseases, and complete resistance to *Diplocarpon rosae*. As typical of many *Rosa* hybrid varieties, flowers are susceptible to *Botrytis* at the end of the season. Typically average resistance to normal pests of *Rosa* hybrid garden plants.

Temperature tolerance: Good heat tolerance, flowers can show signs of fading earlier in high heat, with no other negative effects.

What is claimed is:

1. A new and distinct cultivar of *Rosa* hybrid plant named 'GRAsuper' as herein illustrated and described.

* * * * *